(12) United States Patent
Limaye (10) Patent No.: US 9,931,473 B2
(45) Date of Patent: Apr. 3, 2018

(54) SAFETY PEN NEEDLE ASSEMBLY

(71) Applicant: BECTON, DICKINSON AND COMPANY, Franklin Lakes, NJ (US)

(72) Inventor: Amit Uday Limaye, Wayne, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 365 days.

(21) Appl. No.: 13/920,454

(22) Filed: Jun. 18, 2013

(65) Prior Publication Data
US 2013/0281937 A1    Oct. 24, 2013

Related U.S. Application Data

(63) Continuation of application No. 13/096,121, filed on Apr. 28, 2011, now Pat. No. 8,491,535.

(51) Int. Cl.
*A61M 5/32* (2006.01)
*A61M 5/34* (2006.01)

(52) U.S. Cl.
CPC ........ *A61M 5/3202* (2013.01); *A61M 5/3243* (2013.01); *A61M 5/347* (2013.01); *A61M 2005/3247* (2013.01); *A61M 2005/3254* (2013.01)

(58) Field of Classification Search
CPC ............... A61M 5/3202; A61M 5/002; A61M 2005/3254; A61M 5/3243; A61M 5/5086; A61M 2005/312; A61M 39/20; A61M 5/150572
See application file for complete search history.

(56) References Cited

U.S. PATENT DOCUMENTS

| | | | |
|---|---|---|---|
| 2,371,086 A * | 3/1945 | Watson | A61M 5/282 604/192 |
| 3,021,942 A * | 2/1962 | Hamilton | A61M 5/3202 206/365 |
| 3,967,621 A | 7/1976 | Schwarz | |
| 4,743,233 A | 5/1988 | Schneider | |
| 4,826,490 A | 5/1989 | Byrne et al. | |
| 4,915,697 A * | 4/1990 | Dupont | A61M 5/326 604/192 |
| 4,927,019 A | 5/1990 | Haber et al. | |
| 5,964,731 A | 10/1999 | Kovelman | |
| 7,001,364 B1 | 2/2006 | Farhi | |

(Continued)

FOREIGN PATENT DOCUMENTS

| | | |
|---|---|---|
| EP | 0 356 810 A2 | 3/1990 |
| GB | 2 202 748 A | 10/1988 |

(Continued)

*Primary Examiner* — Emily Schmidt
(74) *Attorney, Agent, or Firm* — Dickinson Wright PLLC (57) ABSTRACT

In one aspect, a safety pen needle assembly is provided which includes a hub having an open proximal end, a needle fixed to the hub having a distal end, and a shield moveably mounted to the hub so as to be movable relative to the hub to selectively cover the distal end of the needle. An interface is defined between the shield and the hub which is sufficiently sealed so as to define a sterility barrier which prevents ingress of contaminants through the interface. At least one sterility barrier is mounted directly to, and across, an open proximal end of the hub and an open distal end of the shield.

18 Claims, 7 Drawing Sheets

(56) References Cited

U.S. PATENT DOCUMENTS

| | | | | |
|---|---|---|---|---|
| 2003/0144633 A1* | 7/2003 | Kirchhofer | ......... | A61M 5/2033 604/201 |
| 2004/0254538 A1* | 12/2004 | Murphy | ............ | A61B 17/8816 604/181 |
| 2005/0171485 A1 | 8/2005 | Larsen et al. | | |
| 2010/0042047 A1 | 2/2010 | Suzuki | | |
| 2011/0066114 A1* | 3/2011 | McDown | ............ | A61M 5/3245 604/192 |

FOREIGN PATENT DOCUMENTS

| | | | |
|---|---|---|---|
| JP | S6272367 A | 4/1987 |
| JP | 2003534105 A | 11/2003 |
| JP | 2007509658 A | 4/2007 |
| JP | 2007185499 A | 7/2007 |
| JP | 2008229321 A | 10/2008 |
| JP | 2009101140 A | 5/2009 |

\* cited by examiner

SAFETY PEN NEEDLE ASSEMBLY

CROSS-REFERENCE TO RELATED APPLICATION

This application is a continuation of U.S. application Ser. No. 13/096,121, filed Apr. 28, 2011, now allowed, the entire contents of which are incorporated herein.

FIELD OF THE INVENTION

This invention relates to safety pen needle assemblies.

BACKGROUND OF THE INVENTION

Safety pen needle assemblies are well known in the art for use with medical injectors, particularly pen injectors. Shielding of a used needle post-injection is provided by such devices. Various configurations for shielding are available, including a displaceable shield relative to the needle hub. U.S. Pat. No. 5,964,731 to Kovelman discloses a shield threaded onto a needle hub. With this configuration, however, the shield must be in its most extreme lowest position, wherein the needle is maximally exposed, for mounting onto a medical injector. As such, a user may inadvertently suffer a needle stick during mounting. Transmission of biological material or disease is not a concern with the needle being in a clean state; however, with a practitioner suffering a needle stick, the pen needle assembly must be disposed of since the needle can not be used subsequently on a patient.

SUMMARY OF THE INVENTION

In one aspect, a safety pen needle assembly is provided which includes a hub, a needle fixed to a transverse wall of the hub, and a shield formed to at least partially telescope over the hub. An outer ablumenal surface of the hub and an inner lumenal surface of the shield are formed with cooperating thread elements to permit relative rotation between the hub and the shield. In an initial state, the cooperating thread elements are in threaded engagement with the shield being positioned relative to the hub with a distal end of the shield sidewall being located distally of a distal end of the needle. Also, in the initial state, the shield and the hub are configured with a rotation-resistance arrangement which inhibits relative rotation between the hub and the shield. The rotation-resistance arrangement is surmountable to allow relative rotation between the hub and the shield with an at least threshold amount of torque being applied, the threshold amount of torque being greater than required to mount the pen needle assembly onto an injector body. Advantageously, with the subject invention, a safety pen needle assembly can be provided having a shield threaded onto a hub with the assembly being mountable with the needle being in a shielded state. This minimizes the possibility of needle stick during mounting of the safety pen needle assembly.

Additionally, a safety pen needle assembly is provided having: a hub with an open proximal end; a needle fixed to the hub, the needle having a distal end, formed for insertion into a patient, and a proximal end; and, a shield moveably mounted to the hub so as to be moveable relative to the hub to selectively cover the distal end of the needle, the shield having an open distal end. An interface is defined between the shield and the hub, which is sufficiently sealed by portions of one or both of the hub and the shield so as to define a sterility barrier which prevents ingressive contaminants through the interface. Also, at least one removable sterility barrier is mounted across the open proximal end of the hub and the open distal end of the shield. Advantageously, with the subject invention, a safety pen needle assembly can be provided which does not require any additional packaging for storage or transportation. With a sterility barrier being defined between the shield and the hub, and the removable sterility barrier being provided to seal open portions of the shield and hub, a fully sealed pen needle assembly is provided.

As used herein, the term "distal", and derivatives thereof, refers to a direction towards a patient during use. The term "proximal", and derivatives thereof, refers to a direction away from a patient during use.

These and other features of the invention will be better understood through a study of the following detailed description and accompanying drawings.

DETAILED DESCRIPTION OF THE INVENTION

With reference to the Figures, a safety pen needle assembly 10 is shown which generally includes a hub 12, a needle 14, and a shield 16. The safety pen needle assembly 10 is formed for mounting onto various injector bodies I and is particularly well-suited for use with pen injectors.

The hub 12 includes a tubular side wall 18 which defines a lumen 20, with an inner lumenal surface 22 and an outer ablumenal surface 24, and a proximal opening 23. A transverse wall 26 extends transversely from the side wall 18 to overlap at least a portion of the lumen 20. Preferably, the transverse wall 26 overlaps completely the lumen 20. The lumenal surface 22 is formed with features 28 for mounting the hub 12 onto the injector body I. Preferably, the mounting features 28 is a thread element formed for threaded engagement with a cooperating thread on the injector body I. As will be appreciated by those skilled in the art, the features 28 may include additional or different features, such as mechanical locking elements (bayonet-type locking elements, snapable locking elements) and/or surface configurations, such as for friction fit, e.g., a Luer configuration.

Figures 1, 2, 3, 4:
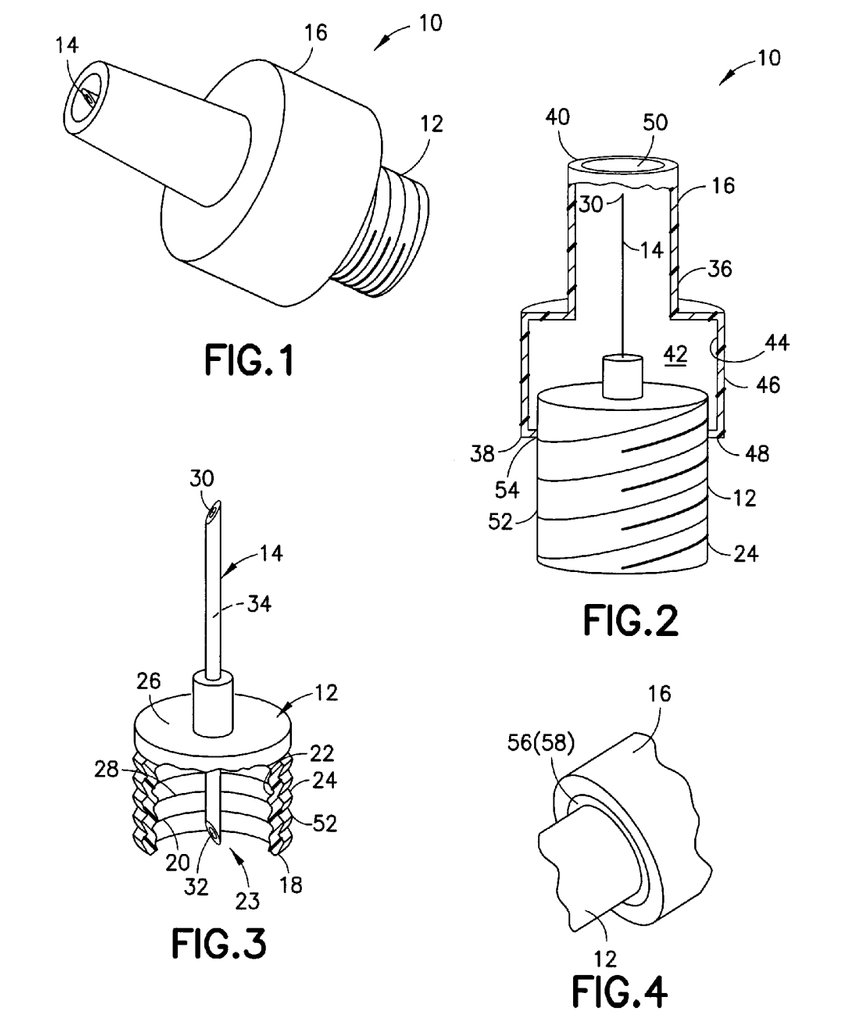
FIG. 1 is a perspective view of a safety pen needle assembly formed in accordance with the subject invention in an initial state.
FIG. 2 is a schematic of a safety pen needle assembly of FIG. 1 in an initial state.
FIG. 3 is a partial cross-sectional view of a hub useable with the subject invention.
FIGS. 4-7 show different rotation-resistance arrangements useable with the subject invention.

The needle 14 is fixed to the transverse wall 26 using any known technique, including adhesive or insert molding. As best shown in FIG. 3, the needle 14 includes a distal end 30, formed for insertion into a patient, and a proximal end 32. A lumen 34 extends between, and is in communication with, the distal and proximal ends 30, 32. The needle 14 is fixed such that the distal end 30 is located distally of the transverse wall 26 and that the proximal end 32 is located proximally of the transverse wall 26.

The shield 16 is generally tubular and includes a shield side wall 36 which extends between proximal and distal ends 38, 40, respectively. The shield side wall 36 is formed to at least partially telescope over the hub 12, as shown in FIG. 2. The shield side wall 36 defines a shield lumen 42 with an inner shield lumenal surface 44 and an outer shield ablumenal surface 46. The proximal end 38 of the shield side wall 36 defines proximal opening 48, in which the hub 12 is nestingly received, and the distal end 40 defines distal opening 50, formed large enough to permit passage therethrough of the needle 14 as described below.

The ablumenal surface 24 of the hub 12 and the shield lumenal surface 44 are formed with cooperating thread elements 52, 54 which permit relative rotation between the hub 12 and the shield 16.

In an initial state, as shown in FIGS. 1 and 2, the shield 16 is positioned relative to the hub 12 with the distal end 40 of the shield side wall 36 being located distally of the distal end 30 of the needle 14. As such, the needle 14 is covered by the shield 16 in the initial state.

The hub 12 and the shield 16 are configured with a rotation-resistance arrangement 56 which inhibits relative rotation between the hub 12 and the shield 16, particularly from the initial state. The rotation-resistance arrangement 56 is surmountable to allow relative rotation between the hub 12 and the shield 16 with an at least threshold amount of torque being applied therebetween. The threshold amount of torque is to be greater than the amount of torque required to mount the safety pen needle assembly 10 onto the injector body I.

Figure 5:
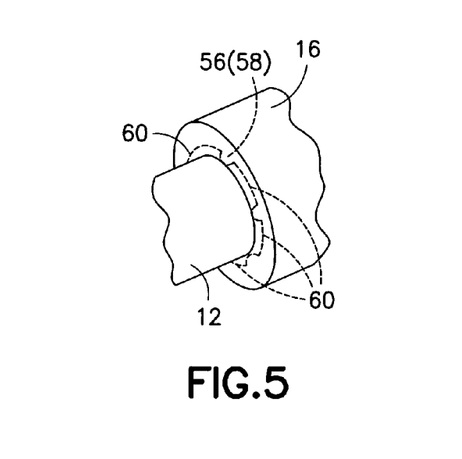

The rotation-resistance arrangement 56, as will be appreciated by those skilled in the art, can be provided in various arrangements. For example, as shown in FIG. 4, the rotation-resistance arrangement 56 may be defined by one or more points of securement 58 formed by adhesion, welding and/or fusion. The points of securement 58 may be continuous or discontinuous about the hub 12. The points of securement 58 may be ruptured, or otherwise caused to fail, with application of the threshold amount of torque between the hub 12 and the shield 16. The one or more points of securement 58 may be also defined by portions integrally formed with the hub 12 and/or the shield 16, such as by injection molding (FIG. 5). The hub 12 and the shield 16 may be integrally formed together with the one or more points of securement 58 being configured to fail upon the threshold amount of torque being applied between the hub 12 and the shield 16, such as by providing the one or more points of securement 58 as thinned or weakened sections and/or providing perforations 60 (shown in dashed lines), or other discontinuities, in between the points of securement 58.

Figure 6:
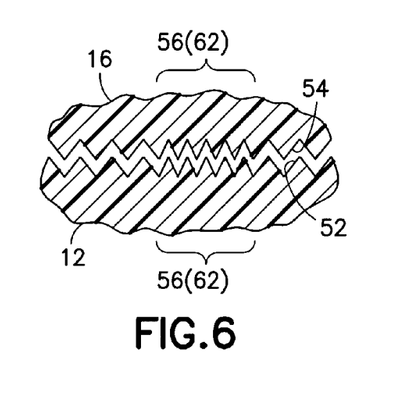

The rotation-resistance arrangement 56 may be also achieved by a frictional or mechanical configuration, whereby an increased amount of torque is required to overcome a higher friction area or mechanical combination. For example, select portions 62 (FIG. 6) of the cooperating thread elements 52, 54 may be formed to have higher frictional engagement, such as by greater surface interaction, deeper thread interengagement, and so forth where the higher frictional engagement may be overcome by application of the threshold amount of torque between the hub 12 and the shield 16. For example, the select portions 62 may define narrower threads than surrounding portions of the cooperating thread elements 52, 54. In this manner, the portions 62 are in tighter engagement than surrounding portions of the cooperating thread elements 52, 54. With rotational displacement, upon sufficient application of torque, the portions 62 disengage apart and rotate to engage the adjacent wider threads, thereby easing the initial tightness of the engagement between the portions 62.

Figure 7:
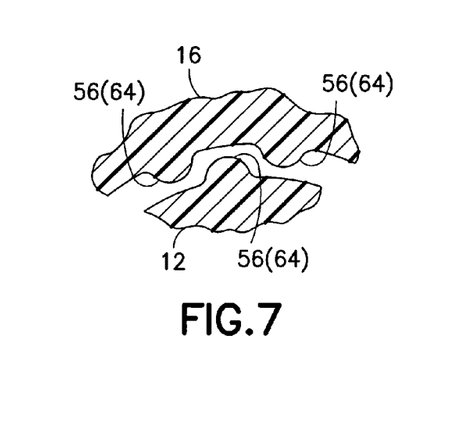

Cooperating locking elements 64 (FIG. 7) may be also provided to act as a mechanical interconnection, such as, for example, snap detents. With sufficient application of torque, the cooperating locking elements 64 may be disengaged, such as, for example, snap release of the snap detents. As will be appreciated by those skilled in the art, the various configurations described herein for the rotation-resistance arrangement 56 may be used singularly or in various combinations.

Figure 8:
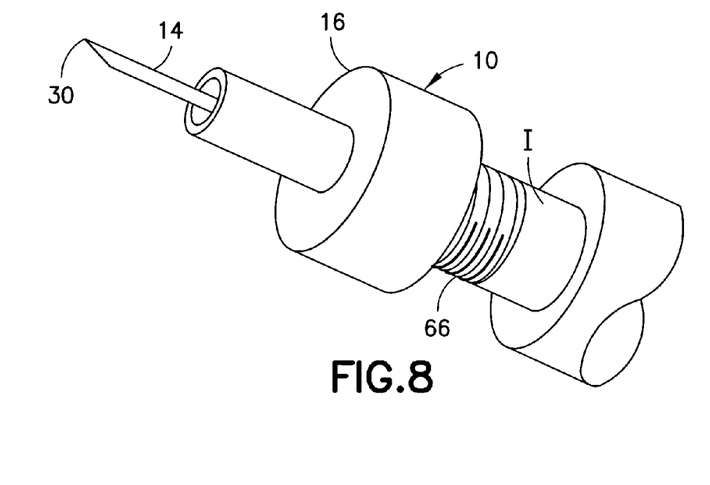
FIG. 8 is a perspective view of a safety pen needle assembly in a ready-to-use state mounted on an injector body.

During use, with reference to FIG. 8, the safety pen needle assembly 10 is mounted onto the injector body I with handling of the shield 16. Rotational force is applied to the safety pen needle assembly 10 so as to cause the features 28 to engage cooperating features 66 on the injector body I. With the torque threshold required to surmount the rotation-resistance arrangement 56 being greater than the torque required to mount the safety pen needle assembly 10 onto the injector body I, the torque applied to the shield 16 is directly transmitted to the hub 12 with the shield 16 and the hub 12 rotating in concert together. With the hub 12 being fully mounted onto the injector body I, and continued application of torque to the shield 16, the rotation-resistance arrangement 56 may be overcome with relative rotation between the shield 16 and the hub 12 being achieved. The cooperating thread elements 52, 54 are configured to permit proximal movement of the shield 16 relative to the hub 12 during mounting so as to permit exposure of the distal end 30 of the needle 14. Preferably, the features 28 in the form of a thread have the same angular orientation as the cooperating thread elements 52, 54 to permit rotation by a user in a single direction to both achieve mounting of the safety pen needle assembly 10 onto the injector body I and proximal displacement of the shield 16 relative to the hub 12.

Figure 9:
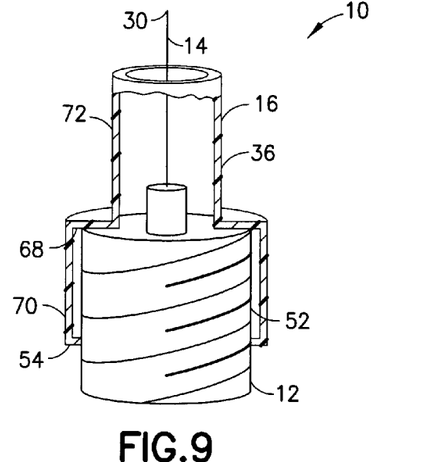
FIG. 9 is a schematic of a safety pen needle assembly of FIG. 8 in a ready-to-use state.
Figure 11:
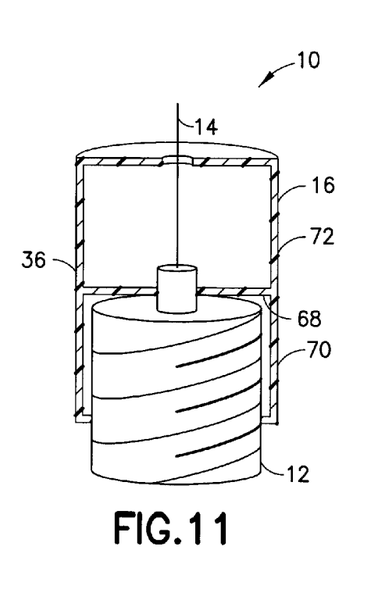
FIG. 11 is a schematic of a safety pen needle assembly formed in accordance with the subject invention using a different shield configuration.
Figure 12:
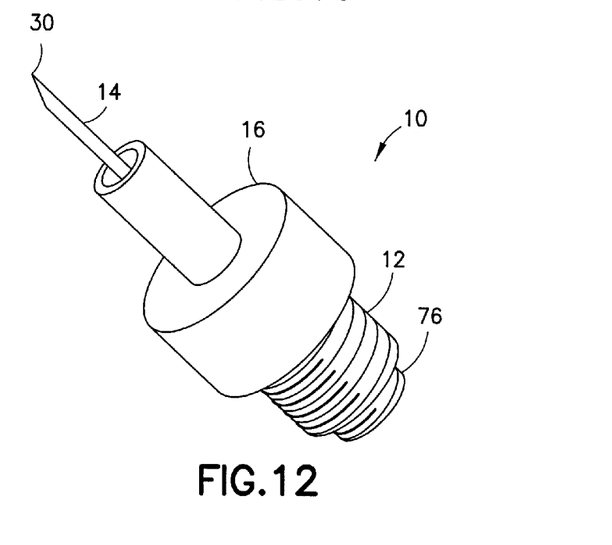
FIG. 12 is a schematic of a safety pen needle assembly formed in accordance with the subject invention utilizing a secondary shield for a proximal end of a needle.
Figure 13:
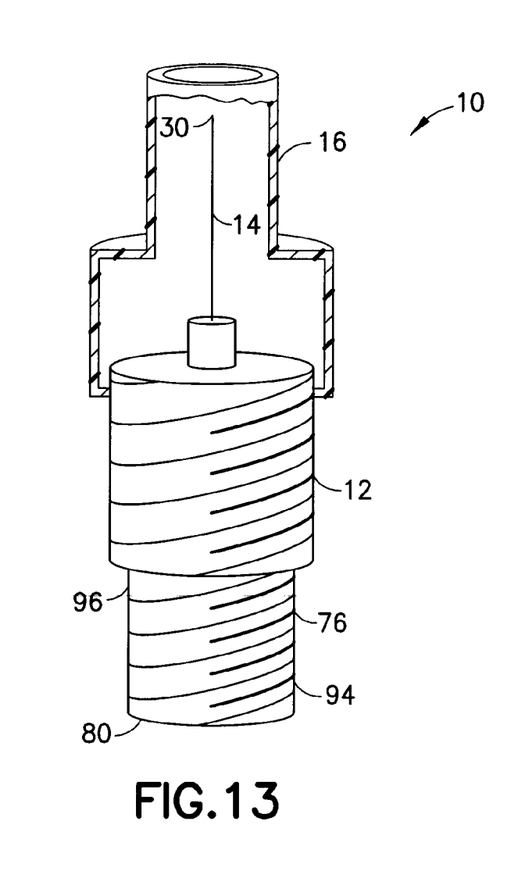
FIG. 13 is a schematic of a safety pen needle assembly of FIG. 12 in post-use state.

With reference to FIGS. 8 and 9, with proximal displacement of the shield 16, the needle 14, particularly the distal end 30, becomes exposed through the distal opening 50 and ready for use. It is preferred that the shield 16 be rotated until it bottoms out. To control the extent of displacement of the shield 16 relative to the hub 12, it is preferred that a stop be provided. With reference to FIGS. 8 and 9, it is preferred that a shoulder 68 be defined in the shield side wall 36 which is formed to interferingly engage against the hub 12 upon sufficient proximal displacement of the shield 16 relative to the hub 12. As shown particularly in FIGS. 8 and 9, the shoulder 68 may define a transition in the shield side wall 36 between a larger diameter proximal section 70 and a smaller diameter distal section 72. Alternatively, as shown in FIG. 11, the proximal and distal sections 70, 72 may be formed with generally the same diameter, with the shoulder 68 protruding inwardly from the shield side wall 36.

Figure 10:
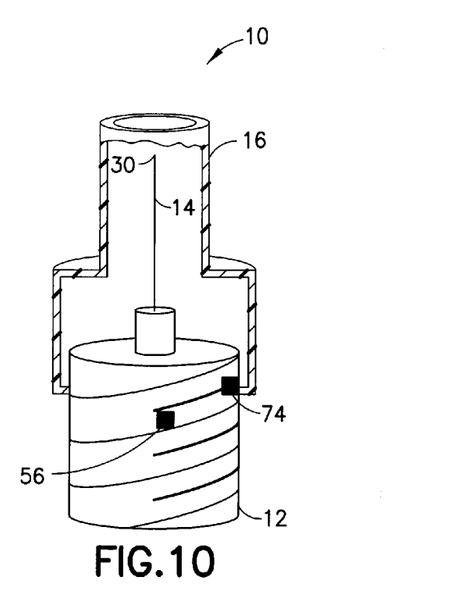
FIG. 10 is a schematic of a safety pen needle assembly formed in accordance with the subject invention in a post-use state.

After use, the shield 16 is caused to rotate in a reverse direction so as to displace the shield 16 distally relative to the hub 12 into a shielded state, as shown in FIG. 10. It is preferred that a locking arrangement 74 be provided which locks the shield 16 relative to the hub 12 in the shielding position. The locking arrangement 74 may be cooperating snap or ramped elements which permit one-way rotation therepast, with resistance against reverse rotation. As will be appreciated by those skilled in the art, various configurations may be utilized.

To permit both displacement from an initial shielded state, as shown in FIGS. 1 and 2, and to achieve a locked shielded state, as shown in FIG. 10, it is preferred that the locking arrangement 74 be configured to be engaged with the shield 16, relative to the hub 12, being located distally of the position of the shield 16 in the initial state. More particularly, it is preferred that the locking arrangement 74 be located distally of the rotation-resistance arrangement 56. Thus, with displacement of the shield 16 from the use state to the post-use state, the rotation-resistance arrangement 56 may be bypassed. With sufficient distal displacement of the shield 16 relative to the hub 12, the locking arrangement 74 is caused to engage and lock the shield 16 in the shielding state relative to the hub 12.

With reference to FIGS. 12-15, it is additionally possible to provide the safety pen needle assembly 10 with a secondary shield 76 configured for shielding the proximal end 32 of the needle 14. The secondary shield 76 is at least partially disposed in the lumen 34 of the hub 12. The secondary shield 76 includes a secondary shield side wall 78 which extends between proximal and distal ends 80, 82, respectively. The secondary shield side wall 78 defines a secondary shield lumen 84 with an inner secondary shield lumenal surface 86 and an outer secondary shield ablumenal surface 88. The proximal end 80 of the secondary shield side wall 78 defines proximal opening 90, formed large enough to permit passage therethrough of the needle 14, as described below.

The lumenal surface 22 of the hub 12 and the secondary shield ablumenal surface 88 are formed with secondary cooperating thread elements 92, 94 which permit relative rotation between the hub 12 and the secondary shield 76.

To permit mounting of the safety pen needle assembly 10 onto the injector body I with use of the secondary shield 76, the features 28 for mounting onto the injector body I are formed on the secondary shield lumenal surface 86, as opposed to the lumenal surface 22 of the hub 12.

Figure 14:
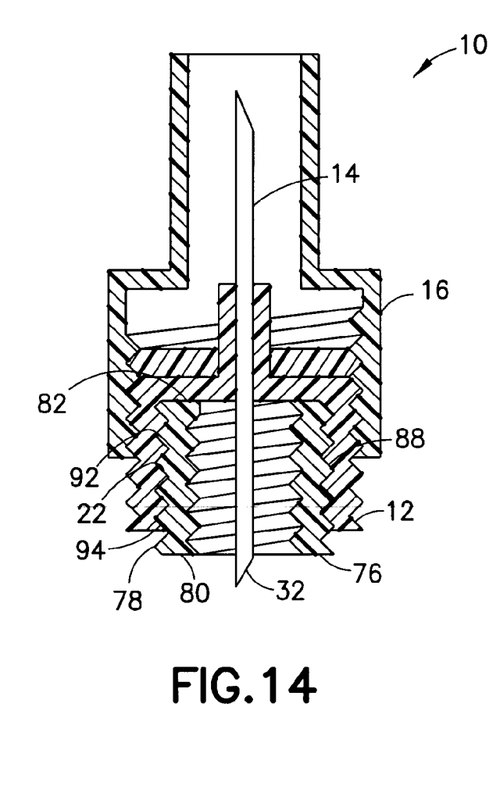
FIG. 14 is a cross-sectional view of a safety pen needle assembly of FIG. 12 in an initial state with the proximal end of the needle exposed.

In an initial state, the secondary shield 76 is preferably positioned relative to the hub 12 with the proximal end 80 of the secondary shield side wall 78 being located proximally of the proximal end 32 of the needle 14. As such, the proximal end 32 of the needle 14 is covered by the secondary shield 76 in the initial state. As shown in FIG. 14, in the initial state, it is preferred that the secondary shield 76 be located in a distalmost position relative to the hub 12. In this manner, the secondary shield 76 is bottomed out relative to the hub 12 and not capable of further distal displacement relative to the hub 12. Alternatively, as shown in FIG. 14, the secondary shield 76 may be formed with the proximal end 80 being located distally of the proximal end 32 of the needle 14 so as to not cover the proximal end 32 of the needle 14 and permit unobstructed visual access thereof.

It is also preferred that the secondary cooperating thread elements 92, 94 have the same angular orientation as the features 28 such that the secondary shield 76 is not displaced proximally relative to the hub 12 during mounting onto the injector body I.

Figure 15:
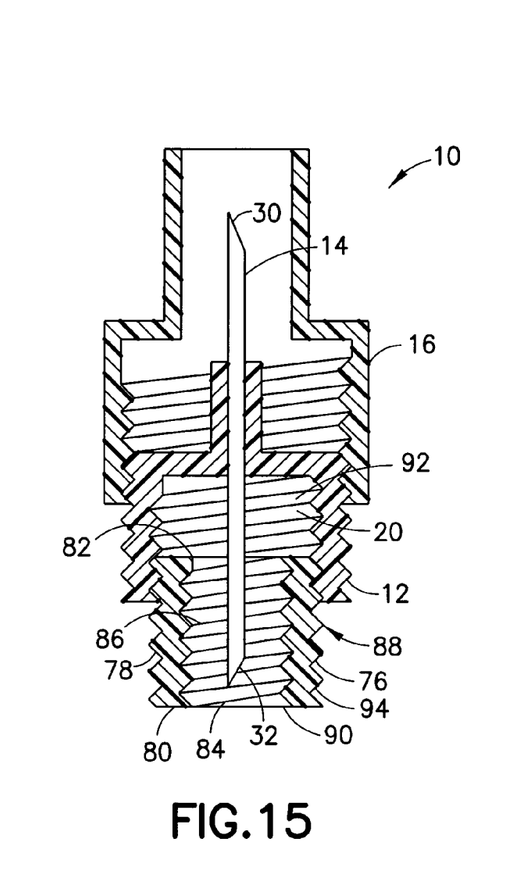
FIG. 15 is a cross-sectional view of a safety pen needle assembly of FIG. 12 in a post-use state.

After use, the safety pen needle assembly 10 is caused to rotate in a reverse direction for dismounting from the injector body I. This results in proximal displacement of the secondary shield 76 relative to the hub 12, as shown in FIG. 15. A secondary locking arrangement 96, configured in similar fashion to the locking arrangement 74, may be provided to lock the secondary shield 76 in a shielding position relative to the hub 12. In particular, in the shielding position, the proximal end 80 of the secondary shield side wall 78 would be located proximally of the proximal end 32 of the needle 14. Alternatively, the secondary locking arrangement 96 need not be utilized. The secondary cooperating thread elements 92, 94 may be configured to allow for maximum extent of proximal displacement of the secondary shield 76 relative to the hub 12 coinciding with the secondary shield 76 shielding the proximal end 32 of the needle 14 after use.

During dismount, initial torque applied to the safety pen needle assembly 10 results in the proximal extension of the secondary shield 76 relative to the hub 12 to the shielding state. Subsequent application of torque results in the shield 16 being displaced distally relative to the hub 12 to the shielding position covering the distal end 30 of the needle 14 in the same manner as described above. As shown in FIG. 15, further application of torque results in the dismounting of the safety pen needle assembly 10 in a fully shielded state from the injector body I with both the distal and proximal ends 30, 32 of the needle 14 being shielded.

Figure 17:
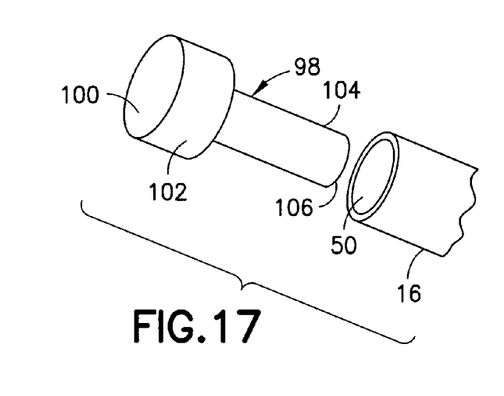
FIGS. 17-20 show a cap or plug useable with the subject invention.
Figure 18:
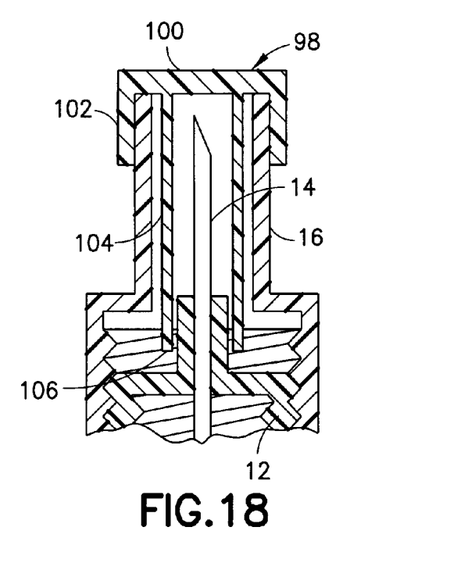
Figure 19:
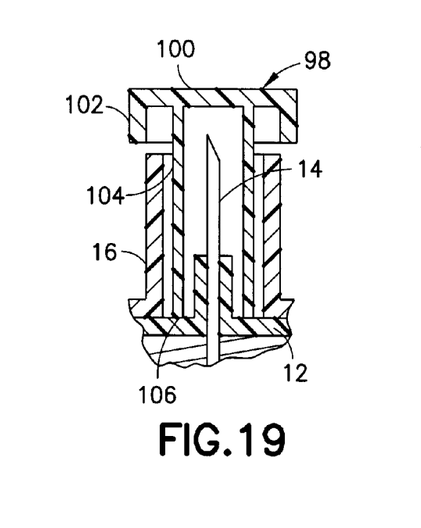

With reference to FIGS. 17-20, the safety pen needle assembly 10 may be provided with a cap or plug for sealing the distal opening 50 in the shield 16 and/or the proximal opening 23 in the hub 12. As will be appreciated by those skilled in the art, various cap or plug configurations may be utilized. With reference to FIGS. 17-19, a cap 98 is shown for sealing the distal opening 50 in the shield 16. The cap 98 includes a base 100 from which extends a rim 102 located about a stem 104. The rim 102 and/or the stem 104 are formed to frictionally engage the shield 16 so as to provide retentive force for the cap 98 to be maintained on the shield 16. The cap 98 may be formed of any resilient material, such as elastomeric or thermoplastic material, which would sufficiently tightly engage the shield 16 so as to define a seal of sufficient integrity to prevent the ingress of contaminants into the shield 16, particularly through the distal opening 50.

The stem 104 is formed generally cylindrical so as to encompass, without contacting, the needle 14. The stem 104 terminates at a stop edge 106. The length of the stem 104 from the base 100 to the stop edge 106 is selected such that the stop edge 106 is caused to engage the hub 12 with sufficient proximal displacement of the shield 16 relative to the hub 12. It is preferred that the full proximal displacement of the shield 16 relative to the hub 12 results in at least partial disengagement of the cap 98 from the shield 16. In this manner, removal of the cap 98 from the shield 16 is facilitated. By way of non-limiting example, and with reference to FIGS. 18-19, with the rim 102 being in frictional engagement with the shield 16, the rim 102 and the stem 104 may be configured such that full proximal displacement of the shield 16 relative to the hub 12 causes full disengagement of the shield 16 from the rim 102 (FIG. 19). As will be appreciated by those skilled in the art, full disengagement is not required in that partial disengagement reduces frictional interengagement and still facilitates separation of the cap 98 from the shield 16. This also applies where the stem 104 is in friction engagement with the shield 16 since frictional interengagement between the two may be reduced by proximal displacement of the shield 16 relative to the hub 12.

Figure 20:
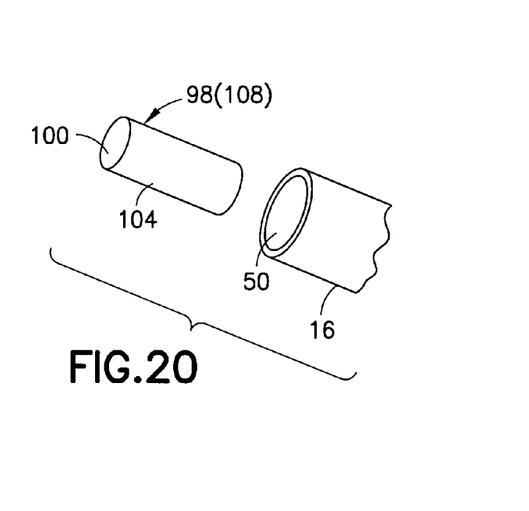

With reference to FIG. 20, it is noted that the cap 98 may be provided in the form of a plug 108 where the base 100 and the stem 104 are provided, but no rim 102. The plug 108 may be configured to perform in the same manner as the cap 98.

Figure 21:
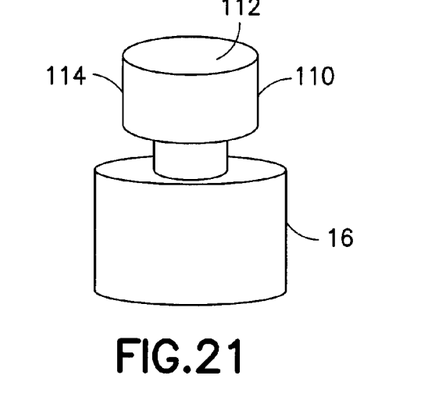
FIGS. 21-22 show a snap-on cap useable with the subject invention.
Figure 22:
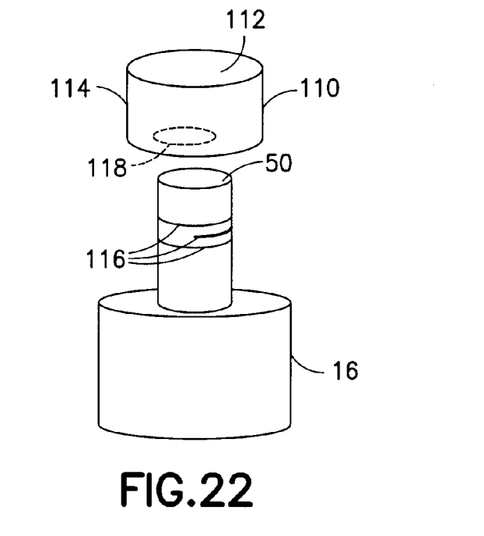

With reference to FIGS. 21-22, a snap-on cap 110 may be provided for sealing the proximal opening 23 and/or the distal opening 50. The snap-on cap 110 includes a base 112 from which protrudes a skirt 114. The snap-on cap 110 may be secured to the shield 16 or the hub 12 by frictional engagement with the skirt 114. To enhance the retentive force, detents 116 may be provided on the shield 16 or the hub 12 onto which the snap-on cap 110 engages. Further, one or more cooperating detents 118 may be provided on the skirt 114 to further enhance the holding force. Two of the snap-on caps 110 may be simultaneously provided with one for sealing the proximal opening 23 and the second for sealing the distal opening 50. It is preferred that the snap-on cap 110 engage the shield 16 or the hub 12 with sufficient force to provide a seal with sufficient integrity to prevent ingress of contaminants into the safety pen needle assembly 10.

Figure 23:
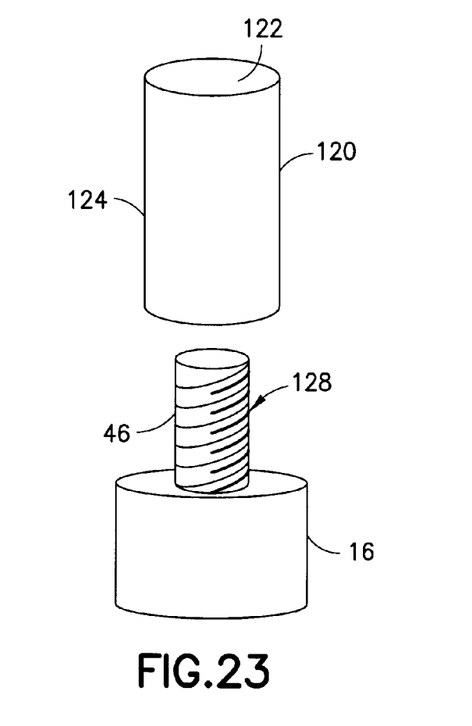
FIGS. 23-24 show an end cap useable with the subject invention.
Figure 24:
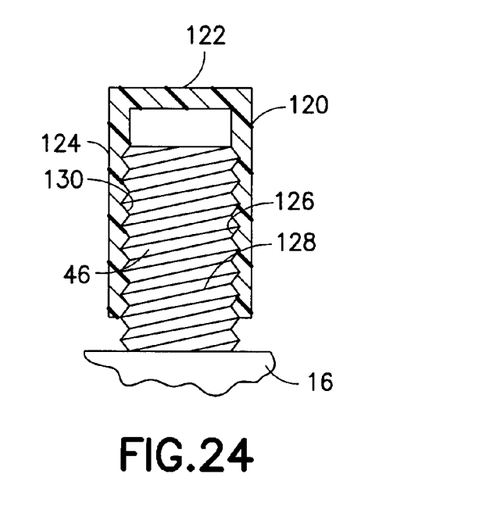

With reference to FIGS. 23-24, an end cap 120 is shown for sealing the distal opening 50 in the shield 16. The end cap 120 includes a base 122 from which protrudes a tubular sidewall 124. Cooperating thread elements 126, 128 are formed on the inside of the sidewall 124 and the shield ablumenal surface 46 so as to permit relative rotation between the end cap 120 and the shield 16. It is further preferred that the cooperating thread elements 126, 128 have an opposing angular rotation to the cooperating thread elements 52, 54. It is also preferred that a rotation-resistance arrangement 130 be provided which inhibits relative rotation between the end cap 120 and the shield 16. The rotation-resistance arrangement 130 may be formed in similar fashion to the rotation-resistance arrangement 56, described above. The rotation-resistance arrangement 130 is surmountable to allow relative rotation between the end cap 120 and the shield 16 with an at least threshold amount of torque being applied therebetween. Preferably, the threshold amount of torque is to be greater than the amount of torque required to mount the safety pen needle assembly 10 onto the injector body I and greater than the amount of torque required to surmount the rotation-resistance arrangement 56. In this manner, torque may be applied to the end cap 120 so as to permit full mounting of the safety pen needle assembly 10 onto the injector I and full proximal displacement of the shield 16 relative to the hub 12, prior to overcoming the rotation-resistance arrangement 130 to permit distal displacement of the end cap 120 relative to the shield 16 and ultimate separation therefrom.

Figure 16:
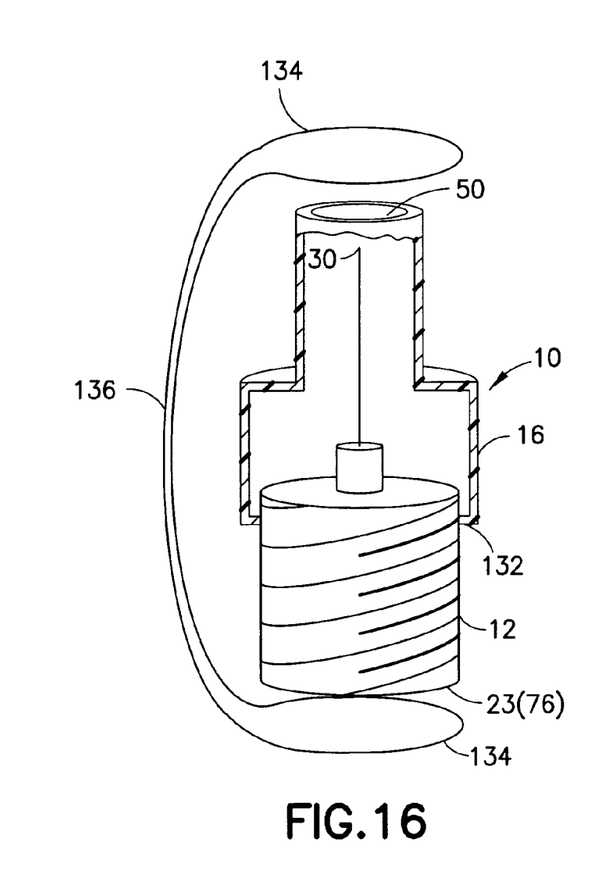
FIG. 16 is a schematic of a safety pen needle assembly formed in accordance with the subject invention in a packaged state.

With reference to FIG. 16, as a further invention, the safety pen needle assembly 10 may be packaged for shipping and transportation without any external casing or packaging. In particular, with reference to FIG. 16, the safety pen needle assembly 10 is provided with the shield 16 being movably mounted to the hub 12 so as to selectively cover the distal end 30 of the needle 14. The shield 16 may be movably mounted to the hub 12 in any manner including, but not limited to, the manner described above. An interface 132 is defined between the hub 12 and the shield 16. Preferably, the shield 16 is in a shielding state initially with the distal end 30 being shielded by the shield 16. The interface 132 is sufficiently sealed by portions of the hub 12 and/or the shield 16 so as to define a sterility barrier which prevents ingress of contaminants through the interface 132.

The interface 132 may be sealed by various techniques, as will be appreciated by those skilled in the art. Preferably, the interface 132 is sealed by a continuous barrier, such as provided by the points of securement 58 described above. It is preferred that the points of securement 58 extend continuously across the interface 132 without disruption. As described above, the points of securement 58 may be defined by adhesion, welding, fusion and/or integral portions of the hub 12 and/or the shield 16. With the interface 132 being sealed, the hub 12 and the shield 16 form a continuous body impervious to the passage of contaminants therethrough. Openings may be provided in the hub 12 and/or the shield 16, such as the distal opening 50 in the shield 16, the proximal opening 23 in the hub 12 and/or the proximal opening 90 in the secondary shield 76. At least one removable sterility barrier 134 is mounted directly to, and across, each of the openings so as to define a sterility barrier therefor. Any peelable sterility barrier, e.g. film-based, may be utilized. Thus, as shown in FIG. 16, the distal opening 50 and the proximal opening 23 or 90 are each provided with at least one of the sterility barriers 134. It is preferred that the sterility barriers 134 be removable, such as by peeling. It is possible to have the sterility barriers 134 be rupturable to provide use of the safety pen needle assembly 10.

For ease of removal, one or more straps 136 may be provided which connect two or more of the sterility barriers 134 so as to enable removal of the sterility barriers 134 in groups of two or more. In this fashion, it is possible to remove all of the sterility barriers 134 as a single unit.

What is claimed is:

1. A safety pen needle assembly comprising:
   a hub having a tubular side wall defining a lumen with a threaded inner luminal surface, a threaded outer ablumenal surface and an open proximal end;
   a needle fixed to said hub, said needle having a distal end for insertion into a patient, and a proximal end extending into said threaded inner luminal surface of said hub;
   a shield having a thread that is engaged to said hub so as to be manually movable relative to said hub via said threaded outer ablumenal surface to selectively expose said distal end of said needle via proximal movement of said shield and cover said distal end of said needle via distal movement of said shield, said shield maintaining threaded engagement to said hub when exposing and covering said distal end of said needle, said shield having an open distal end, wherein an interface is defined between said shield and said hub, said interface being sufficiently sealed so as to define a sterility barrier which prevents ingress of contaminants through said interface; and
   at least one sterility barrier mounted directly to, and across, said open proximal end of said hub and said open distal end of said shield,
   wherein a spring for moving said shield relative to said hub is not provided within said assembly; and
   wherein when said distal end of said needle is exposed before, during and after needle insertion, said shield is held in a first position.

2. A safety pen needle assembly as in claim 1, wherein said interface is sealed by a continuous barrier.

3. A safety pen needle as in claim 2, wherein said continuous barrier is defined by one or more selected from the group consisting of adhesion, welding, fusion, portions of said hub, and portions of said shield.

4. A safety pen needle assembly as in claim 1, wherein said at least one sterility barrier comprises at least one first sterility barrier mounted to said open proximal end of said hub and at least one second sterility barrier mounted to said open distal end of said shield.

5. A safety pen needle assembly as in claim 4, further comprising one or more straps connecting said at least one first sterility barrier and said at least one second sterility barrier.

6. A safety pen needle assembly as in claim 1, wherein said at least one sterility barrier is removable.

7. A safety pen needle assembly as in claim 6, wherein said proximal end of said needle does not extend beyond threads of said threaded inner luminal surface.

8. A safety pen needle assembly as in claim 1, wherein said at least one sterility barrier includes film.

9. A safety pen needle assembly as in claim 1, wherein said at least one sterility barrier is rupturable.

10. A safety pen needle assembly as in claim 1, wherein the hub includes a transverse wall extending transversely from the side wall to overlap at least a portion of the lumen.

11. A safety pen needle assembly as in claim 1, wherein the shield includes a shield side wall extending between proximal and distal ends, the shield side wall being formed to at least partially telescope over the hub, the shield side wall defining a shield lumen with an inner shield luminal surface.

12. A safety pen needle assembly as in claim 1, further comprising locking means for locking the shield relative to the hub with the distal end of the shield side wall being located distally of the distal end of the needle.

13. A safety pen needle assembly as in claim 1, wherein said threaded inner luminal surface is configured for threaded engagement with an injector body.

14. A safety pen needle assembly as in claim 1, wherein when the distal end of the needle is covered, the shield is held in a second position.

15. A safety pen needle assembly as in claim 14, wherein a user manually adjusts a position of the shield between the first position and the second position.

16. A safety pen needle assembly as in claim 15, wherein the shield can be manually adjusted and held in a third position that is between the first position and the second position.

17. A safety pen needle assembly as in claim 1, wherein said at least one sterility barrier being peelable.

18. A safety pen needle assembly comprising:
a hub having an open proximal end;
a needle fixed to said hub, said needle having a distal end, formed for insertion into a patient, and a proximal end;
a shield movably mounted to said hub so as to be movable relative to said hub to selectively cover said distal end of said needle, said shield having an open distal end, wherein an interface is defined between said shield and said hub, said interface being sufficiently sealed so as to define a sterility barrier which prevents ingress of contaminants through said interface; and
at least one sterility barrier mounted directly to, and across, said open proximal end of said hub and said open distal end of said shield,
wherein, in an initial state, the shield and the hub are configured with a rotation-resistance arrangement which inhibits relative rotation between the hub and the shield, the rotation-resistance arrangement being surmountable to allow relative rotation between the hub and the shield with at least a threshold amount of torque being applied therebetween, the threshold amount of torque being greater than that required to mount the safety pen needle assembly onto an injector body.

* * * * *